US006127406A

United States Patent [19]

Gunasekera et al.

[11] Patent Number: 6,127,406

[45] **Date of Patent: *Oct. 3, 2000**

[54] DISCODERMOLIDE COMPOUNDS AND METHODS OF USE

[75] Inventors: Sarath P. Gunasekera; Ross E. Longley, both of Vero Beach, Fla.

[73] Assignee: Harbor Branch Oceanographic Institution, Inc., Ft. Pierce, Fla.

[ * ] Notice: This patent is subject to a terminal disclaimer.

[21] Appl. No.: 09/412,552

[22] Filed: Oct. 5, 1999

Related U.S. Application Data

[60] Provisional application No. 60/103,806, Oct. 9, 1998.

[51] Int. Cl.[7] .................... A61K 31/35

[52] U.S. Cl. .................... 514/459; 549/292

[58] Field of Search .................... 514/459; 549/292

[56] References Cited

U.S. PATENT DOCUMENTS

| | | | |
|---|---|---|---|
| 4,206,221 | 6/1980 | Miller et al. | 424/278 |
| 4,808,590 | 2/1989 | Higa et al. . | |
| 4,939,168 | 7/1990 | Gunasekera et al. | 514/459 |
| 4,960,790 | 10/1990 | Stella et al. | 514/449 |
| 5,010,099 | 4/1991 | Gunasekera et al. | 514/459 |
| 5,157,049 | 10/1992 | Haugwitz et al. | 514/449 |
| 5,681,847 | 10/1997 | Longley et al. | 514/459 |
| 5,789,605 | 8/1998 | Smith, III et al. | 514/459 |

FOREIGN PATENT DOCUMENTS

| | | |
|---|---|---|
| 2280677 | 8/1995 | United Kingdom . |
| 9824429 | 6/1998 | WIPO . |
| 9824427 | 11/1998 | WIPO . |

OTHER PUBLICATIONS

Nerenberg, Jennie B., Deborah T. Hung, Patricia K. Somers, Stuart L. Schreiber (1993) "Total Synthesis of the Immunosuppressive Agent (–)–Discodermolide" *J. Am. Chem. Soc.* 115:12621–12622.

Hung, Deborah T., Jie Chen, Stuart L. Schreiber (1996) "(+)–Discodermolide binds to microtubules in stoichiometric ratio to tubulin dimers, blocks taxol binding and results in mitotic arrest" *Chemistry & Biology* 3(4):287–293.

Hung, Deborah T., Jennie B. Nerenberg, Stuart L. Schreiber (1994) "Distinct binding and cellular properties of synthetic (+)–and (–)–discodermolides" *Chemistry & Biology* 1(1):67–71.

Haar, Ernst ter, Herbert S. Rosenkranz, Ernest Hamel, Billy W. Day (1996) "Computational and Molecular Modeling Evaluation of the Structural Basis for Tubulin Polymerization Inhibition by Colchicine Site Agents" *Bioorganic & Medicinal Chemistry* 4(10):1659–1671.

Faulkner, D. John (1998) *Natural Products Reports* 15:113–158.

Harried, Scott S., Ge Yang, Marcus A. Strawn, David C. Myles (1997) "Total Synthesis of (–)–Discodermolide: An Application of a Chelation–Controlled Alkylation Reaction" *J. Org. Chem.* 62:6098–6099.

Smith, III, Amos B., Yuping Qiu, David R. Jones, Kaoru Kobayashi (1995) "Total Syntheses of (–)–Discodermolide" *J. Am. Chem. Soc.* 117:12011–12012.

Gunasekera, Sarath P., Malika Gunasekera, Ross E. Longley (1990) "Discodermolide: A New Bioactive Polyhydroxylated Lactone from the Marine Sponge *Discodermia dissoluta*" *J. Org. Chem.* 55:4912–4915.

Gunasekera, Sarath P., Malika Gunasekera, Ross E. Longley (1991) *J. Org. Chem.* 56(3):1346. Additions and Corrections to 1990, vol. 55 above.

Stafford, Jeffrey A. and Mukund M. Mehrotra (1995) "Total Synthesis of the Immunosuppressive Agent (–)–Discodermolide—Distinct Binding and Cellular Properties of Synthetic (+)–and (–)–Discodermolide" *Organic Chemistry* 8:41–47.

Uemura, D. et al. (1985) "Norhalichondrin A: An Antitumor Polyether Macrolide from a Marine Spone" *J. Am. Chem. Soc.* 107:4796–4798.

Faulkner, D.J. (1987) "Marine Natural Products" *Natural Products Reports* 4:539–576.

Fuchs, D.A., R.K. Johnson (1978) "Crtologic Evidence that Taxol, an Antineoplastic Agent from *Taxus brevifolia*, Acts as a Mitotic Spindle" *Cancer Treatment Reports* 62(8):1219–1222.

Schiff, P.B. et al. (1979) "Promotion of microtubule assembly in vitro by taxol" *Nature* (London) 22:665–667.

Rowinsky, E.K., R.C. Donehower (1995) "Paclitaxel (Taxol)" *The New England Journal of Medicine* 332(15:1004–1014.

Minale, L. et al. (1976) "Natural Products from Porifera" *Fortschr. Chem. org. Naturst.* 31:1–72.

Kelly–Borges et al. (1994) "Species Differentiation in the Marine Sponge Genus Discodermia (Demospongiae: Lithistida): the Utility of Ethanol Extact Profiles as Species–Specific Chemotaxonomic Markers" *Biochemical Systematics and Ecology* 22(4):353–365.

*Primary Examiner*—Amelia Owens

*Attorney, Agent, or Firm*—Saliwanchik, Lloyd & Saliwanchik

[57] ABSTRACT

Novel analogs of compounds from the marine sponge *Discodermia dissoluta* have been prepared. These compounds have been shown to have activity against mammalian cancer cells, and can be used in treating human patients which host cancer cells, including leukemia, melanoma, breast, colon, CNS, renal, ovarian, prostate, and lung tumors.

16 Claims, No Drawings

DISCODERMOLIDE COMPOUNDS AND METHODS OF USE

CROSS-REFERENCE TO A RELATED APPLICATION

This application claims priority from provisional application U.S. Ser. No. 60/103,806, filed Oct. 9, 1998.

The subject invention was made with government support under a research grant supported by NIH/NCI Grant No. 1R01CA74227. The government has certain rights in this invention.

FIELD OF THE INVENTION

This invention relates to organic compounds and compositions which have useful therapeutic properties. More particularly, the invention concerns novel discodermolide compounds having immunomodulatory and antitumor activities, pharmaceutical compositions comprising such compounds, methods for the preparation of the novel compounds, and compositions and methods of their use for therapeutic purposes.

BACKGROUND OF THE INVENTION

Also of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed.

In searching for new biologically active compounds, it has been found that some natural products and organisms are potential sources for chemical molecules having useful biological activity of great diversity. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1998)*Natural Products Reports* 15:113–158; Gunasekera, S. P., M. Gunasekera, R. E. Longley and G. K. Schulte (1990) "Discodermolide: A new bioactive polyhydroxy lactone from the marine sponge *Discodermia dissoluta*" *J. Org. Chem.*, 55:4912–4915; (1991) *J. Org. Chem.* 56:1346; Hung, Deborah T., Jenne B. Nerenberg, Stuart Schreiber (1994) "Distinct binding and cellular properties of synthetic (+)- and (–)discodermolides" *Chemistry and Biology* 1:67–71; Hung, Deborah T., Jie Cheng, Stuart Schreiber (1996) (+)-Discodermolide binds to microtubules in stoichiometric ratio to tubulin dimers, blocks taxol binding and results in mitotic arrest" *Chemistry and Biology* 3:287–293; Nerenberg, Jennie B., Deborah T. Hung, Patricia K. Somers, Stuart L. Schreiber (1993) "Total synthesis of immunosuppressive agent (–)-discodermolide" *J. Amer. Chem. Soc.* 115:12621–12622; Smith III, Amos B., Yuping Qiu, David R. Jones, Karoru Kobayashi (1995) "Total synthesis of (–) discodermolide" *J. Amer. Chem. Soc.* 117:12011–12012; Harried, Scott H., Ge Yang, Marcus A. Strawn, David C. Myles (1997) "Total synthesis of (–)-discodermolide: an application of a chelation-controlled alkylation reaction" *J. Org. Chem.* 62:6098–6099 and references cited therein. U.S. Patent No. 4,808,590 discloses compounds, having antiviral, antitumor, and antifungal properties, isolated from the marine sponge Theonella sp.

BRIEF SUMMARY OF THE INVENTION

A principal object of this invention is the provision of novel compositions of biologically active discodermolide compounds which can advantageously be used for immunomodulation and/or treating cancer. In a specific embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting tumors in a host include contacting tumor cells with an effective amount of the new pharmaceutical compositions of the invention. The tumor cells inhibited by the invention are those which are susceptible to the subject compounds described herein or compositions comprising those compounds.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

The subject invention provides novel compositions of biologically active discodermolide compounds which are useful for immunomodulation and/or treating cancer. More specifically, the novel compounds, compositions and methods of use can advantageously be used to inhibit the growth of tumor cells in a mammalian host. More particularly, the subject compounds can be used for inhibiting in a human the growth of tumor cells, including cells of breast, colon, CNS, ovarian, renal, prostate, or lung tumors, as well as human leukemia or melanoma cells. As described herein, the discodermolide analogs of the subject invention can be used to treat a variety of cancers.

These compounds have utility for use in the treatment of cancer, and as microtubulin polymerizers. Most preferably, the invention comprises a method for the antitumor treatment of a human in need of such treatment, i.e., a human hosting cancer cells, including breast, colon, lung, leukemia, central nervous system cancer, melanoma, ovarian, renal and prostate cancer.

In accordance with the subject invention, preparation of certain acetylated derivatives of discodermolide, specifically, acetylation at C-3 or C-7 for monoacetates and C-3 and C-7 for diacetates improves their antitumor and microtubule polymerizing activities compared to that of the non-acetylated compound, discodermolide, and thus increases their utility for the treatment of human cancers. The subject invention includes the exemplified compounds as well as analogs, variants, and derivatives thereof.

In accordance with the invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

Seven new discodermolide analogs and the previously reported discodermolide tetraacetate have been prepared by partial acetylation of discodermolide with acetic anhydride in pyridine at room temperature. The resulting complex mixture was separated by HPLC in a $SiO_2$ column using a mixture of MeOH and $CH_2Cl_2$. The acetylated products were identified by NMR spectral analysis and their structures were confirmed by mass spectral analysis.

Certain discodermolide analogs were shown to have improved antitumor and microtubule polymerizing abilities (compounds 4, 7, and 8) compared to the non-acetylated discodermolide compound. This result demonstrates the importance of acetylation at C-3 or C-7 for monoacetates and C-3 and C-7 for diacetate derivatives for improving the anticancer activity of the compound. Other described analogs have reduced antitumor and microtubule polymerizing activities compared to discodermolide, indicating that acetylation at C-11 and C-17 inhibit the antitumor activity of discodermolide and demonstrates the importance of C-11 and C-17 in the antitumor activity of discodermolide.

In one embodiment, the objects of the invention are accomplished by the provision of the biologically active compounds that have a structure according to the formula (I), below:

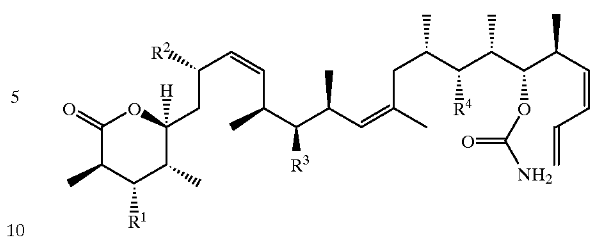

Particularly preferred embodiments are discodermolide acetates: where R=$CH_3$

| | | R1 | R2 | R3 | R4 |
|---|---|---|---|---|---|
| (1) | 3,7,11,17-tetraacetyldiscodermolide | RCOO | RCOO | RCOO | RCOO |
| (2) | 3,7,17-triacetyldiscodermolide | RCOO | RCOO | OH | RCOO |
| (3) | 3,7,11-triacetyldiscodermolide | RCOO | RCOO | RCOO | OH |
| (4) | 3,7-diacetyldiscodermolide | RCOO | RCOO | OH | OH |
| (5) | 3,11-diacetyldiscodermolide | RCOO | OH | RCOO | OH |
| (6) | 3,17-diacetyldiscodermolide | RCOO | OH | OH | RCOO |
| (7) | 3-acetyldiscodermolide | RCOO | OH | OH | OH |
| (8) | 7-acetyldiscodermolide | OH | RCOO | OH | OH |

Additional embodiments are discodermolide acetates: where R=$CH_3$

| | R1 | R2 | R3 | R4 |
|---|---|---|---|---|
| 11-acetyldiscodermolide | OH | OH | RCOO | OH |
| 17-acetyldiscodermolide | OH | OH | OH | RCOO |
| 7,11-diacetyldiscodermolide | OH | RCOO | RCOO | OH |
| 7,17-diacetyldiscodermolide | OH | RCOO | OH | RCOO |
| 11,17-diacetyldiscodermolide | OH | OH | RCOO | RCOO |
| 3,11,17-triacetyldiscodermolide | RCOO | OH | RCOO | RCOO |
| 7,11,17-triacetyldiscodermolide | OH | RCOO | RCOO | RCOO |

Various enantiomers of the discodermolides, as defined above, can be synthesized by persons of ordinary skill in the art. The natural discodermolide isolated from marine sponges is predominantly found to be the (+) enantiomer.

In preferred embodiments of the invention, the compounds are substantially pure, i.e., contain at least 95% of the compound as determined by established analytical methods.

Discodermolide compounds and methods of preparing those compounds or compositions comprising them, are described in U.S. Pat. Nos. 4,939,168, 5,010,099, 5,681,847, and 5,840,750, which are hereby incorporated by reference.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

As used in this application, the terms "analogs," "variants" and "derivatives" refer to compounds which are substantially the same as another compound but which may have been modified by, for example, adding additional side groups. The terms “analogs,” “variants” and “derivatives” as used in this application also refer to compounds which are substantially the same as another compound but which have atomic or molecular substitutions at certain locations in the compound.

As embodied and fully described herein, the invention also comprises methods of use of the new compounds and compositions of the invention, e.g., methods of improving immune responses and methods of inhibiting tumors and other cancer cells in an animal, preferably a mammal. Most preferably, the invention comprises a method for the anti-tumor treatment of a human in need of such treatment, i.e., a human hosting cancer cells, including breast, colon, or lung tumor cells, or leukemia cells. In addition to the types of cancer cells listed above for which the subject discodermolides and compositions are particularly useful, the subject compounds have also been shown to be useful for their antiproliferative activity against certain CNS cancer cell lines, melanoma cell lines, ovarian cancer cell lines, renal cancer cell lines, and prostate cancer cell lines. It would be expected, based on the particular antiproliferative modes of action identified herein, that additional cancer cell lines would also be inhibited by these compounds.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Preparation, Purification, and Identification of Discodermolide Acetates

Discodermolide (3.5 mg) was treated with dry pyridine (1.0 mL) and acetic anhydride (10 $\mu$L) in a small reacti-vial and the mixture was stirred at 45° C. for 8 hours. The reaction mixture was evaporated under a stream of nitrogen and the residue (~3.7 mg) was re-dissolved in dichlomethane for HPLC studies.

HPLC separation of the acetate mixture:

The product was subjected to HPLC on a $SiO_2$ (5 $\mu$m, Phenomenex semi-prep Lichrosorb) column using a mixture of 6% MeOH in $CH_2Cl_2$ and separated into two fractions. The less polar fraction was re-chromatographed using the same HPLC column with 3% MeOH in $CH_2Cl_2$, and separated in to six pure compounds (24SG511→24SG516). The polar fraction was re-chromatographed using the same HPLC column with 4% MeOH in $CH_2Cl_2$ to yield pure 24SG611.

In an additional example, discodermolide (8.0 mg) was treated with dry pyridine (1.0 mL) and acetic anhydride (10 $\mu$L) in a small reacti-vial and stirred the mixture at 18° C. for 15 hours. The reaction mixture was evaporated under a stream of nitrogen and the residue was subjected to HPLC on a $SiO_2$ (5 $\mu$m, Phenomenex semi-prep Lichrosorb) column using a mixture of 5% MeOH in $CH_2Cl_2$ to yield pure 25SG714 (8) in addition to other discodermolide acetates (1–7).

| Identification No. | Yield | Structure |
|---|---|---|
| 24SG511 | 0.8 mg | Discodermolide-3,7,11,17-tetraacetate (1) |
| 24SG512 | 0.3 mg | Discodermolide-3,7,17-triacetate (2) |
| 24SG513 | 0.8 mg | Discodermolide-3,7,11-triacetate (3) |
| 24SG514 | 0.6 mg | Discodermolide-3,7-diacetate (4) |
| 24SG515 | 0.2 mg | Discodermolide-3,11-diacetate (5) |
| 24SG516 | 0.2 mg | Discodermolide-3,17-diacetate (6) |
| 24SG611 | 0.2 mg | Discodermolide-3-acetate (7) |
| 25SG741 | 0.2 mg | Discodermolide-7-acetate (8) |

| Structure | Molecular Formula | Molecular Weight by HRFABMS |
|---|---|---|
| Discodermolide-3,7,1 1,17-tetraacetate (1) | $C_{41}H_{63}NO_{12}$ | m/z = 702.420 (M + CH3COO)$^+$ |
| Discodermolide-3,7,17-triacetate (2) | $C_{39}H_{61}NO_{11}$ | m/z = 742.405 (M + Na)$^+$ |
| Discodermolide-3,7,11-triacetate (3) | $C_{39}H_{61}NO_{11}$ | m/z = 742.410 (M + Na)$^+$ |
| Discodermolide-3,7-diacetate (4) | $C_{37}H_{59}NO_{10}$ | m/z = 700.418 (M + Na)$^+$ |
| Discodermolide-3,11-diacetate (5) | $C_{37}H_{59}NO_{10}$ | m/z = 678.418 (M + H)$^+$ |
| Discodermolide-3,17-diacetate (6) | $C_{37}H_{59}NO_{10}$ | m/z = 678.419 (M + H)$^+$ |
| Discodermolide-3-acetate (7) | $C_{35}H_{57}NO_9$ | m/z = 636.411 (M + H)$^+$ |
| Discodermolide-7-acetate (8) | $C_{35}H_{57}NO_9$ | m/z = 636.412 (M + H)$^+$ |

-continued

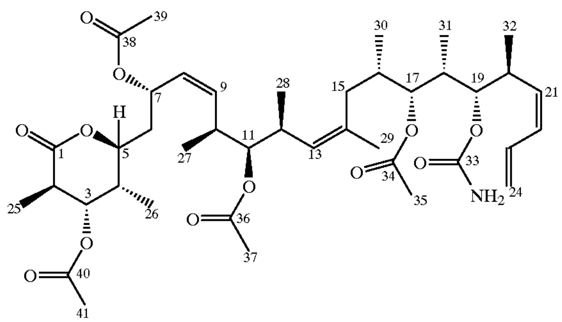

Numbering system $^1$H NMR Data of compounds 1 → 4 in $CDCl_3$

| Pos. | Compound 1 δ 1H (mult., J in Hz) | Compound 2 δ 1H (mult., J in Hz) | Compound 3 δ 1H (mult., J in Hz) | Compound 4 δ 1H (mult., J in Hz) |
|---|---|---|---|---|
| 2 | 2.66(dq, 5.8, 7.3) | 2.70(dq, 5.8, 7.4) | 2.73(dq, 5.8, 7.4) | 2.72(dq, 5.8, 7.5) |
| 3 | 4.83(dd 4.3, 4.2) | 4.88(dd, 4.2, 4.2) | 4.89(dd, 4.1, 4.1) | 4.88(dd, 4.1, 5.8) |
| 4 | 2.09(m) | 2.05(m) | 2.08(m) | 2.06(m) |
| 5 | 4.22(dt, 1, 5, 9.7) | 4.32(dt, 1.5, 9.7) | 4.30(dt, 1.5, 9.7) | 4.35(dt 1.5, 9.7) |
| 6 | 2.10(ddd, 8.3, 9.7, 12.6) | 2.10(m) | 2.10(ddd, 8.3, 9.7, 12.6) | 2.10(m) |
| 6 | 1.64(ddd, 3.2, 9.7, 12.6) | 1.78(ddd, 3.2, 9.7, 12.6) | 1.70(ddd, 3.2, 9.7, 12.6) | 1.81(ddd, 3.2, 9.5, 14.8) |
| 7 | 5.61(dt, 3.2, 8.9) | 5.72(dt 3.2, 8.9) | 5.72(dt, 3.2, 8.9) | 5.74(3.2, 9.0, 14.8) |
| 8 | 5.21(dd, 9.0, 10.7) | 5.35(dd, 7.8, 10.3) | 5.27(dd, 9.0, 10.7) | 5.37(dd, 9.0, 10.8) |
| 9 | 5.42(dd, 10.7, 10.7) | 5.45(dd, 9.1, 10.3) | 5.44(dd, 10.7, 10.7) | 5.45(dd, 10.2, 10.8) |
| 10 | 2.79(ddq, 6.1, 6.9, 10.7) | 2.72(ddq, 6.1, 6.5, 10.3) | 2.89(ddq, 6.1, 6.9, 10.7) | 2.73(ddq, 6.1, 6.5, 10.2) |
| 11 | 4.58(dd, 6.1, 5.1) | 3.12(dd, 5.2, 6.5) | 4.70(dd, 5.6, 5.6) | 3.18(m) |
| 12 | 2.44(ddq, 5.1, 6.6, 9.9) | 2.45(ddq, 5.2, 7.1, 9.7) | 2.63(ddq, 5.1, 6.7, 9.7) | 2.60(ddq, 5.1, 6.7, 9.5) |
| 13 | 4.89(d, 9.9) | 5.16(d, 9.7) | 4.94(d, 9.7) | 5.20(d, 9.5) |
| 15 | 1.80(dd, 12.5, 11.8) | 1.89(dd, 17.0, 12.1) | 1.94(m) | 1.90(m) |
| 15 | 1.61(dd, 12.5, 10.0) | 1.69(dd, 12.1, 1.0) | 1.61(m) | 1.90(m) |
| 16 | 2.00(m) | 2.07(m) | 1.92(m) | 1.88(m) |
| 17 | 4.71(dd, 5.6, 5.8) | 4.79(dd, 5.9, 5.9) | 3.25(ddd, 4.9, 4.9) | 3.27(m) |
| 18 | 1.91(ddq, 5.6, 6.1, 6.8) | 2.01(ddq, 5.9, 6.1, 7.2) | 1.87(m) | 1.85(m) |
| 19 | 4.52(dd, 6.1, 6.1) | 4.61(dd, 6.1, 6.1) | 4.71(dd, 6.1, 6.1) | 4.72(dd, 4.4, 7.2) |
| 20 | 3.07(ddq, 6.1, 6.6, 11.0) | 3.12(ddq, 6.1, 6.9, 10.6) | 3.01(ddq, 6.1, 6.5, 10.4) | 2.97(ddq, 6.2, 6.9, 10.2) |
| 21 | 5.25(ddd, 1.1, 11.0, 10.0) | 5.32(dd, 10.6, 11.0) | 5.29(dd, 10.4, 10.4) | 2.34(dd, 10.6, 11.0) |
| 22 | 5.97(dd, 11.0, 11.0) | 6.02(dd, 11.0, 11.0) | 6.02(dd, 11.0, 11.0) | 6.01(dd, 11.0, 11.0) |
| 23 | 6.65(ddd, 10.2, 11.0, 16.8) | 6.69(ddd, 10.8, 11.0, 16.9) | 6.54(ddd, 9.5, 11.0, 16.8) | 5.60(ddd, 9.6, 11.0, 16.9) |
| 24 | 5.16(d, 16.8) | 5.20(d, 16.9) | 5.14(d, 16.8) | 5.19(d, 16.9) |
| 24 | 5.10(d, 10.2) | 5.14(d, 10.8) | 5.10(d, 9.5) | 5.10(d, 9.6) |
| 25 | 1.24(d, 7.3) | 1.29(d, 7.3) | 1.30(d, 7.4) | 1.30(d, 7.5) |
| 26 | 0.93(d, 6.7) | 0.98(d, 6.5) | 0.98(d, 6.5) | 0.98(d, 6.5) |
| 27 | 0.90(d, 6.9) | 0.98(d, 6.9) | 0.99(6.1) | 0.99(d, 6.5) |
| 28 | 0.80(d, 6.6) | 0.91(d, 7.1) | 0.89(d, 6.7) | 0.94(d, 6.7) |
| 29 | 1.55(s) | 1.62(s) | 1.60(s) | 1.63(s) |
| 30 | 0.63(d, 6.6) | 0.72(d, 6.6) | 0.80(d, 5.8) | 0.82(d, 5.9) |
| 31 | 0.84(d, 6.8) | 0.91(d, 7.2) | 1.00(d, 6.5) | 0.98(d, 6.5) |
| 32 | 0.90(d, 6.9) | 0.97(d, 6.9) | 0.95(d, 6.6) | 0.99(d, 6.5) |
| 35 | 2.04(s) | 2.07(s) | | |
| 37 | 1.97(s) | | 2.01(s) | |
| 39 | 1.96(s) | 2.02(s) | 2.00(s) | 2.02(s) |
| 41 | 2.04(s) | 2.08(s) | 2.09(s) | 2.08(s) |

$^1$H NMR Data of compounds 5 → 8 in $CDCl_3$

| Pos. | Compound 5 (1H (mult., J in Hz) | Compound 6 (1H (mult., J in Hz) | Compound 7 (1H (mult., J in Hz) | Compound 8 δ 1H (mult., J in Hz) |
|---|---|---|---|---|
| 2 | 2.75(dq, 4.5, 7.3) | 2.74(dq, 5.8, 7.4) | 2.74(dq, 4.3, 7.4) | 2.62(dq, 5.8, 7.2) |
| 3 | 4.90(dd, 4.5, 4.3) | 4.89(dd, 4.2, 4.2) | 4.89(dd, 3.9, 4.1) | 3.71(dd, 5.8, 5.8) |
| 4 | 2.09(m) | 2.07(m) | 2.05(m) | 2.04(m) |
| 5 | 4.57(dt, 1, 5, 10.0) | 4.55(dt, 1.5, 9.7) | 4.58(dt, 2.0, 10.1) | 4.40(dt, 1.5, 10.0) |
| 6 | 2.10(m) | 1.82(ddd, 8.3, 9.7, 12.3) | 2.10(m) | 2.02(m) |
| 6 | 1.64(ddd, 3.2, 9.7, 12.6) | 1.70(ddd, 3.2, 9.7, 12.3) | 1.82(ddd, 3.2, 9.7, 12.6) | 1.80(ddd, 3.2, 9.6, 12.5) |
| 7 | 4.75(m) | 4.70(dt 3.2, 8.9) | 4.71(dt, 3.2, 8.7) | 5.70(dt, 3.2, 8.9) |
| 8 | 5.39(dd, 7.8, 10.7) | 5.48(m) | 5.50(dd, 7.8, 10.7) | 5.36(dd, 8.9, 10.3) |
| 9 | 5.42(dd, 10.7, 10.7) | 5.48(m) | 5.42(dd, 10.3, 10.7) | 5.46(dd, 10.3, 10.3) |
| 10 | 2.88(ddq, 6.4, 6.5, 10.7) | 2.74(m) | 2.79(ddq, 5.7, 6.7, 10.3) | 2.75(ddq, 10.3, 7.0) |
| 11 | 4.72(dd, 6.4, 5.5) | 3.13(m) | 3.18(dd, 5.7, 5.7) | 3.19(dd, 7.0, 4.2) |
| 12 | 2.60(ddq, 5.5, 6.6, 10.1) | 2.40(ddq, 5.1, 6.1, 9.9) | 2.56(ddq, 5.7, 7.7, 10.2) | 2.61(m) |
| 13 | 4.94(d, 10.1) | 4.94(d, 9.9) | 5.10(d, 10.2) | 5.19(d, 10.1) |

-continued

| | | | | |
|---|---|---|---|---|
| 15 | 1.79(dd, 12.5, 11.5) | 1.91(m) | 1.89(m) | 1.90(m) |
| 15 | 1.61(m) | 1.63(m) | 1.69(m) | 1.61(m) |
| 16 | 1.89(m) | 2.05(m) | 1.91(m) | 1.90(m) |
| 17 | 3.25(dd, 5.0, 5.5) | 4.78(dd, 5.0, 5.0) | 3.27(ddd, 5.0, 5.9, 5.9) | 3.27(dd, 5.5, 5.5) |
| 18 | 1.85(m) | 2.00(m) | 1.92.(m) | 1.92(m) |
| 19 | 4.61(dd, 6.1, 6.4) | 4.61(dd, 6.1, 6.1) | 4.71(dd, 4.4, 7.2) | 4.69(dd, 7.4, 4.4) |
| 20 | 3.00(ddq, 6.4, 6.5, 10.6) | 3.13(m) | 2.99(ddq, 6.5, 7.2, 10.6) | 2.98(ddq, 7.4, 10.9, 6.5) |
| 21 | 5.25(dd, 10.6, 11.0) | 5.32(dd, 10.6, 10.6) | 5.34(dd, 10.6, 10.6) | 5.36(dd, 10.9, 10.9) |
| 22 | 6.0I(dd, 11.0, 11.0) | 6.02(dd, 10.6, 11.0) | 6.01(dd, 10.6, 11.0) | 6.01(dd, 10.9, 11.0) |
| 23 | 6.61(ddd, 10.2, 11.0, 16.8) | 6.70(ddd 10.1, 11.0, 16.9) | 6.60(ddd, 10.4, 11.0, 16.9) | 6.60(ddd, 11.0, 16.9, 10.2) |
| 24 | 5.24(d, 16.8) | 5.14(d, 16.9) | 5.19(d, 16.9) | 5.21(d, 16.9) |
| 24 | 5.11(d, 10.2) | 5.06(d, 10.1) | 5.15(d, 10.4) | 5.10(d, 10.3) |
| 25 | 1.31(d, 7.3) | 1.30(d, 7.4) | 1.30(d, 7.4) | 1.29(d, 7.2) |
| 26 | 0.97(d, 6.7) | 0.97(d, 6.0) | 0.98(d, 6.5) | 1.03(d, 6.8) |
| 27 | 0.99(d, 6.5) | 1.00(d, 6.7) | 1.00(d, 6.7) | 0.99(d, 7.0) |
| 28 | 0.87(d, 6.6) | 0.98(d, 6.1) | 0.92(d, 7.7) | 0.90(d, 6.8) |
| 29 | 1.62(s) | 1.63(s) | 1.64(s) | 1.63(s) |
| 30 | 0.80(d, 6.6) | 0.71(d, 6.6) | 0.81(d, 6.2) | 0.81(d, 6.0) |
| 31 | 0.97(d, 6.8) | 0.91(d, 6.4) | 0.96(d, 7.2) | 0.97(d, 6.5) |
| 32 | 0.90(d, 6.5) | 0.95(d, 6.6) | 0.98(d, 6.5) | 0.96(d, 6.5) |
| 35 | | 2.07(s) | | |
| 37 | 2.03(s) | | | |
| 39 | | | | 2.01(s) |
| 41 | 2.08(s) | 2.07(s) | 2.08(s) | |

Acylation (OH→OCOR) is achieved by treating the said compound with a mixture of alkyl anhydride or acylhalide and pyridine (1:1) at room temperature overnight or maintaining at 45° C. for 4 to 8 hours.

EXAMPLE 2

Antitumor Effects of Discodermolide and Discodermolide Analogs

Discodermolide and discodermolide analogs were analyzed as to their effects on proliferation of A549 human adenocarcinoma and P388 murine leukemia cell lines. P388 cells were obtained from Dr. R. Camalier, National Cancer Institute, Bethesda, Md., and A549 cells were obtained from American Type Culture Collection, Rockville, Md. All cell lines were maintained in Roswell Park Memorial Institute (RPMI) medium 1640 supplemented with 10% Rehatuin™ fetal calf serum (Intergen Company, Purchase, N.Y.). All cell lines are cultured in plastic tissue culture flasks and kept in an incubator at 37° C. in humidified air containing 5% $CO_2$. Prior to testing, antibiotic-free stock cultures of each of the cell lines were subcultured to $10^6$ cells/ml by dilution in fresh growth medium at 2 to 3 day intervals.

To assess the antiproliferative effects of agents against the P388 cell line, 200 μl cultures (96-well tissue culture plates, Nunc, Denmark) are established at $1\times10^5$ cells/ml in drug-free medium or medium containing the test agent at 10.0, 1.0, 0.10 and 0.010 μg/ml. The solvent for all dilutions is ethanol. All experimental cultures are initiated in medium containing Gentamycin sulfate (50 μg/ml; Schering Corporation, Kenilworth, N.J.).

After 48-hr exposures, P388 cells are enumerated using 3-[4,5-Dimethylthiazol-2-yl]-2,5-diphenyltetrazolium bromide (MTT) (M. C. Alley, et al., Cancer Res. 48:589, 1988). Similar procedures are utilized for A549 cells which require an additional 48 hr exposure prior to MTT addition. Results are expressed as percent inhibition compared to the negative (no drug) control. Positive drug controls are included to monitor drug sensitivity of each of the cell lines. These include varying dilutions of 5-fluorouracil and adriamycin.

To quantitate the effects on cell proliferation and resulting $IC_{50}$ values, 75 μl of warm growth media containing 5 mg/ml MTT is added to each well, cultures returned to the incubator, and left undisturbed for 90 minutes. To spectrophotometrically quantitate formation of reduced formazan, plates are centrifuged (900× g, 5 minutes), culture fluids removed by aspiration, and 200 μl of acidified isopropanol (2 ml concentrated HCl/liter isopropanol) added per well. The absorbance of the resulting solutions is measured at 570 nm with a plate reader (TECAN Spectra II PlateReader, TECAN U.S., Research Triangle Park, N.C.) and a 650 nm reference filter. The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp.316–348, Charles Griffin Co., London, 1978). A linear relationship between tumor cell number and formazan production has been routinely observed over the range of cell densities observed in these experiments. Two standard drug controls are included in each assay as a check to monitor the drug sensitivity of each of the cell lines and $IC_{50}$ values are determined for each drug-cell combination.

The results in Table 1 show discodermolide Analog 4 to be the most active against P388 cells, with an $IC_{50}$ value of 0.7 nM, followed by 8 ($IC_{50}$=4 nM), 7 ($IC_{50}$=9 nM), 5 ($IC_{50}$=103 nM), 3 ($IC_{50}$=166 nM), 1 ($IC_{50}$=837 nM), 6 ($IC_{50}$=1149 nM) and 2 (IC5>6825 nM).

For A549 cells, Analog 8 was also the most active, with an $IC_{50}$ value of 0.8 nM, followed by 4 ($IC_{50}$=3.7 nM), 7 ($IC_{50}$=9.4 nM), 5 ($IC_{50}$=295 nM), 3 ($IC_{50}$=554 nM), 6 ($IC_{50}$=736 nM), 1 ($IC_{50}$=1307 nM) and 2 ($IC_{50}$>1307 nM).

The $IC_{50}$ for (+)discodermolide 9 for P388 was 35 nM and for A549 cells, 34 nM.

TABLE 1

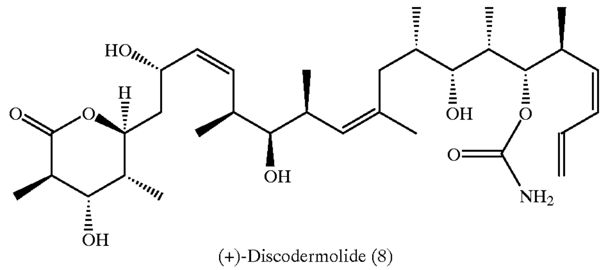

(+)-Discodermolide (8)

| | Cmpd | Sample ID | P388 IC-50 (nM) | A549 IC-50 (nM) | G2/M Block | Concentration (nM) | Microtubule Bundling? | Concentration (nM) | Polymerization? (10 uM, 37 C.) |
|---|---|---|---|---|---|---|---|---|---|
| 3,7,11,17-tetraacetate | 1 | 24SG51-1 | 837 | 1307 | – | 100 | No | 100 | No |
| 3,7,17-triacetate | 2 | 24SG51-2 | >6825 | >1307 | – | 100 | No/No | 100/1000 | No |
| 3,7,11-triacetate | 3 | 24SG51-3 | 166 | 554 | – | 100 | No | 100 | No |
| 3,7-diacetate | 4 | 24SG51-4 | 0.7 | 3.7 | + | 100 | Yes/Yes | 10/100 | Yes |
| 3,11-diacetate | 5 | 24SG51-5 | 103 | 295 | – | 100 | No | 100 | No |
| 3,17-diacetate | 6 | 24SG51-6 | 1149 | 736 | – | 100 | No/Yes | 100/1000 | No |
| 3-acetate | 7 | 24SG61-1 | 9 | 9.4 | + | 100 | Yes/Yes | 10/100 | Yes |
| 7-acetate | 8 | 25SG69-1 | 4 | 0.8 | + | 100 | Yes/Yes | 1000/100 | Yes (6° C.–37° C.) |
| Discodermolide | 9 | | 35 | 34 | + | 100 | Yes/Yes | 10/100 | Yes |
| Paclitaxel | | | | 7.7 | + | 100 | Yes | 100 | Yes |

EXAMPLE 3

Detection of Microtubule Bundling Patterns in Cells by Immunofluorescence

Discodermolide, discodermolide analogs and paclitaxel were evaluated as to their effects on the microtubule network of cells using FITC-labeled, anti-alpha-tubulin monoclonal antibodies. Cells treated with discodermolide or paclitaxel routinely exhibit abnormal formation of multiple centriolar-radiating microtubules with extensive clusters of associated microtubular "bundles", unlike the fine "mesh" of individual microtubules which make up the cytoskeletal network.

On day 1, $2.5\times10^5$ adherent tumor cells were cultured in RPMI 1640 tissue culture medium supplemented with 10% fetal calf serum (TCM) overnight at 37° C. in 5% $CO_2$ on 22 $mm^2$ coverslips in 6-well microtiter plates. On day 2, TCM was removed and replaced with 100 nM discodermolide or analogs or paclitaxel in TCM or TCM without drug (control) and incubated overnight at 37° C. in 5% $CO_2$. On day 3, TCM was removed and cells attached to coverslips were fixed with a 3.7% formaldehyde solution in Dulbecco's PBS for 10 minutes at room temperature. Cells were permeabilized with a 2% Triton X-100 solution, 2 ml per well, for 5 minutes at room temperature and washed twice in Dulbecco's PBS prior to staining.

To each well containing cells attached to coverslips a 2 ml volume of mouse monoclonal anti-alpha-tubulin (Cat # T-5168, Sigma Immuno Chemicals) diluted 1:2400 was added and the cells incubated at 37° C. in 5% $CO_2$ for 45 minutes. Coverslips were rinsed twice with Dulbecco's PBS. A 2 ml volume of goat-anti-mouse-IgG-FITC conjugate (Cat # T-5262, Sigma Immuno Chemicals) diluted at 1:2400 was added and the cells incubated at 37° C. in 5% $CO_2$ for 45 minutes. Coverslips were rinsed once with sterile distilled water and mounted on slides and observed under the microscope using epifluorescence illumination for the presence of abnormal aster and microtubule bundle formation.

Discodermolide9 and paclitaxel both induced the formation of microtubule bundles at 100 nM. Analogs 4, 7, and 8 induced similar microtubule bundle formation at 100 nM. Analog 6 induced microtubule bundles only at 1000 nM. Analogs 1, 2, 3, and 5 were negative in the microtubule bundling assay.

EXAMPLE 4

Effect of Discodermolide and Analogs on Cell Cycle Progression of A549 Human Lung Cells in Comparison to Paclitaxel Cell cycle studies were initiated in order to pinpoint a specific phase within the cell cycle in which discodermolide analogs were exerting their antiproliferative effect. A549 human lung cells were used as cell cycle targets to compare the effects of discodermolide, discodermolide analogs and paclitaxel on perturbation of the cell cycle. Cell cycle analyses were performed as follows: A549 cells were incubated at 37° C. in 10% $CO_2$ in air in the presence or absence of varying concentrations of discodermolide, discodermolide analogs or paclitaxel (purchased from Molecular Probes, Eugene Oreg.) for 48 hr.

Cells were harvested, fixed in ethanol and stained with 0.5 mg/ml of P.I. together with 0.1 mg/ml of RNAse A. This procedure permeabilizes live cells and allows entry of P.I. to stain DNA (propidium iodide also stains double stranded RNA, so RNAse is included in the preparation to exclude this possibility). Stained preparations were analyzed on a Coulter EPICS ELITE with 488 nm excitation with the dead cells excluded by back gating of P.I. preparations without detergent on forward and side scatter histograms. Fluorescence measurements and resulting DNA histograms were collected from at least 5,000 P.I. stained cells at an emission wavelength of 690 nM. Raw histogram data was further analyzed using a cell cycle analysis program (Multicycle, Phoenix Flow Systems). The results of these experiments are shown in Table 1.

Discodermolide9 and discodermolide analogs 4, 7, and 8 induced cell cycle, $G_2$/M block at a concentration of 100 nM. The discodermolide analogs 1, 2, 3, 5 and 6 were negative for cell cycle block when tested at a concentration of 100 nM. Paclitaxel at a concentration of 100 nM was positive for cell cycle, $G_2$/M block.

EXAMPLE 5

Tubulin Polymerization

Polymerization of purified bovine brain tubulin (Cytoskeleton Inc., Denver, Colo.) was followed by changes in the optical density of tubulin solutions at 350 nm in a Hitachi U-3010 spectrophotometer equipped with a SPR-10 electronic thermostatted cell holder. Stock solutions of tubulin were diluted on ice in G-PEM buffer (1 mM GTP, 80 mM PIPES, 1 mM EGTA, 0.5 mM magnesium chloride; pH 6.8) to a final concentration of 1 mg/ml. The instrument was zeroed on this solution at 2° C. Discodermolide, its analogs, or paclitaxel were then added to the tubulin solution to a final concentration of 10 μM, quickly mixed, and the absorbance monitored at 37° C.

The results in Table 1 show that both discodermolide 9 and paclitaxel induced the polymerization of purified tubulin at a concentration of 10 μM at 37° C. Analogs 4, 7, and 8 were both able to induce tubulin polymerization at 10 μM. Analogs 1, 2, 3, 5 and 6 were inactive at 10 μM in the tubulin polymerization assay.

EXAMPLE 6

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for inhibiting the growth of cancer cells, said method comprising administering to said cells an effective amount of an acetylated discodermolide compound.

2. The method, according to claim 1, wherein said compound is mono-acetylated at the C3 or the C7 position.

3. The method, according to claim 1, wherein said compound is di-acetylated at the C3 and C7 positions.

4. The method, according to claim 1, wherein said acetylated discodermolide compound has the following structure:

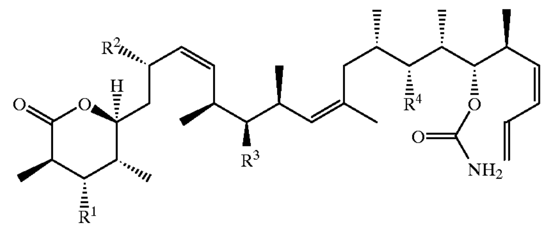

wherein $R^1$, $R^2$, $R^3$, and $R^4$ are independently either RCOO or OH; wherein R is $CH_3$, and wherein either $R^1$ or $R^2$, or both $R^1$ and $R^2$ are RCOO.

5. The method, according to claim 4, wherein said compound is selected from the group consisting of 3-acetyldiscodermolide, 7-acetyeldiscodermolide, and 3, 7-diacetyldiscodermolide.

6. The method, according to claim 1, wherein said cancer cells are selected from the group consisting of human leukemia, lung cancer, colon cancer, CNS cancer, melanoma, ovarian cancer, renal cancer, prostate cancer, and breast cancer.

7. A compound for inhibiting the growth of cancer cells, wherein said compound is an acetylated discodermolide compound.

8. The compound, according to claim 7, wherein said compound is mono-acetylated at the C3 or the C7 position.

9. The compound, according to claim 7, wherein said compound is di-acetylated at the C3 and C7 positions.

10. The compound, according to claim 7, wherein said acetylated discodermolide compound has the following structure:

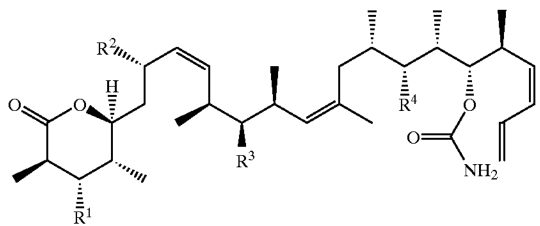

wherein $R^1$, $R^2$, $R^3$, and $R^4$ are independently either RCOO or OH; wherein R is $CH_3$, and wherein either $R^1$ or $R^2$, or both $R^1$ and $R^2$ are RCOO.

11. The compound, according to claim 10, wherein said compound is selected from the group consisting of 3-acetyldiscodermolide, 7-acetyldiscodermolide, and 3, 7-diacetyldiscodermolide.

12. A pharmaceutical composition for inhibiting the growth of cancer cells, said composition comprising an effective amount of an acetylated discodermolide compound and a pharmaceutically acceptable carrier.

13. The pharmaceutical composition, according to claim 1, wherein said compound is mono-acetylated at the C3 or the C7 position.

14. The pharmaceutical composition, according to claim 1, wherein said compound is di-acetylated at the C3 and C7 positions.

15. The pharmaceutical composition, according to claim 1, wherein said acetylated discodermolide compound has the following structure:

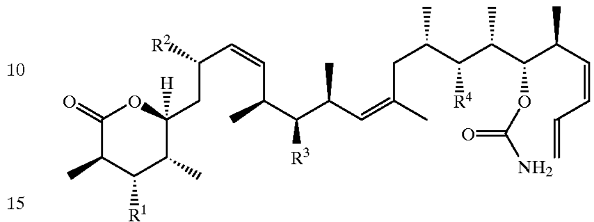

wherein $R^1$ is RCOO; $R^2$, $R^3$, and $R^4$ are independently either RCOO or OH; wherein R is $CH_3$ and wherein either $R^1$ or $R^2$, or both $R^1$ and $R^2$ are RCOO.

16. The pharmaceutical composition, according to claim 4, wherein said compound is selected from the group consisting of 3-acetyldiscodermolide,7-acetyldiscodermolide, and 3, 7-diacetyldiscodermolide.

* * * * *